United States Patent
Lefevre et al.

(10) Patent No.: US 7,611,519 B2
(45) Date of Patent: Nov. 3, 2009

(54) METHODS FOR SELECTING KNEE PROSTHESIS ELEMENTS AND DEVICE THEREFOR

(75) Inventors: Christian Lefevre, 8, Rue Bougainville, Brest (FR) 29200; Eric Stindel, 24, Allee Verte, Locmania Plouzane (FR) 29280; Jean-Louis Briard, 7, Allee des Fougeres, Mont Saint Aignan (FR) 76130; Philippe Merloz, 129, Allee des Ancolies, Saint-Imier (FR) 38330; Michael Breysse, Saint Pierre de Chandieu (FR)

(73) Assignees: Depuy (Ireland) Limited, County Cork (IE); Christian Lefevre, Brest (FR); Eric Stindel, Locmania Plouzane (FR); Jean-Louis Briard, Mont Saint Aignan (FR); Philippe Merloz, Saint-Imier (FR)

( * ) Notice: Subject to any disclaimer, the term of this patent is extended or adjusted under 35 U.S.C. 154(b) by 517 days.

(21) Appl. No.: 10/494,615

(22) PCT Filed: Nov. 4, 2002

(86) PCT No.: PCT/FR02/03770
§ 371 (c)(1),
(2), (4) Date: Nov. 1, 2004

(87) PCT Pub. No.: WO03/039377
PCT Pub. Date: May 15, 2003

(65) Prior Publication Data
US 2005/0049524 A1    Mar. 3, 2005

(30) Foreign Application Priority Data
Nov. 5, 2001    (FR)   ................................ 114287

(51) Int. Cl.
A61B 17/56    (2006.01)

(52) U.S. Cl. .................................. 606/102; 623/20.14
(58) Field of Classification Search ................ 606/102, 606/97, 86 R, 130; 128/922, 923; 600/414, 600/416, 595; 623/20.15, 914, 20.14, 20.19, 623/20.21, 20.24, 20.32, 20.35
See application file for complete search history.

(56) References Cited

U.S. PATENT DOCUMENTS

| | | | |
|---|---|---|---|
| 4,323,534 A | 4/1982 | DesMarais | |
| 4,355,425 A | 10/1982 | Jones et al. | |
| 5,075,173 A | 12/1991 | Benefield et al. | |
| 5,682,886 A | 11/1997 | Wong et al. | |
| 5,824,085 A * | 10/1998 | Sahay et al. | ................ 128/898 |
| 5,959,030 A | 9/1999 | Berta | |

(Continued)

FOREIGN PATENT DOCUMENTS

EP    0472946    3/1992

(Continued)

*Primary Examiner*—Eduardo C Robert
*Assistant Examiner*—David Comstock
(74) *Attorney, Agent, or Firm*—Young & Thompson

(57) ABSTRACT

Method for selecting one or several knee prosthesis elements, by acquiring spatial data concerning spacing and tensioned femorotibial position, including the corresponding HKA angle, for at least three angular positions, of 20°, of 0°, and of the order of 90° in flexion, processing the data thus obtained to verify whether the HKA angles are substantially equal and included within the tolerable limits, and processing the data, in particular those corresponding to extension and flexion of 90° to determine the dimensions and/or positions of the implant.

14 Claims, 1 Drawing Sheet

U.S. PATENT DOCUMENTS

| | | | |
|---|---|---|---|
| 5,962,573 A | 10/1999 | Berta | |
| 6,002,859 A * | 12/1999 | DiGioia et al. | 703/11 |
| 6,013,734 A | 1/2000 | Berta | |
| 6,177,515 B1 | 1/2001 | Smith et al. | |
| 6,433,063 B1 | 8/2002 | Berta | |
| 6,535,756 B1 * | 3/2003 | Simon et al. | 600/424 |
| 6,667,367 B1 | 12/2003 | Berta | |

FOREIGN PATENT DOCUMENTS

| | | |
|---|---|---|
| WO | WO 99 23956 | 5/1999 |
| WO | WO 99 60939 | 12/1999 |
| WO | 03011962 | 2/2003 |

\* cited by examiner

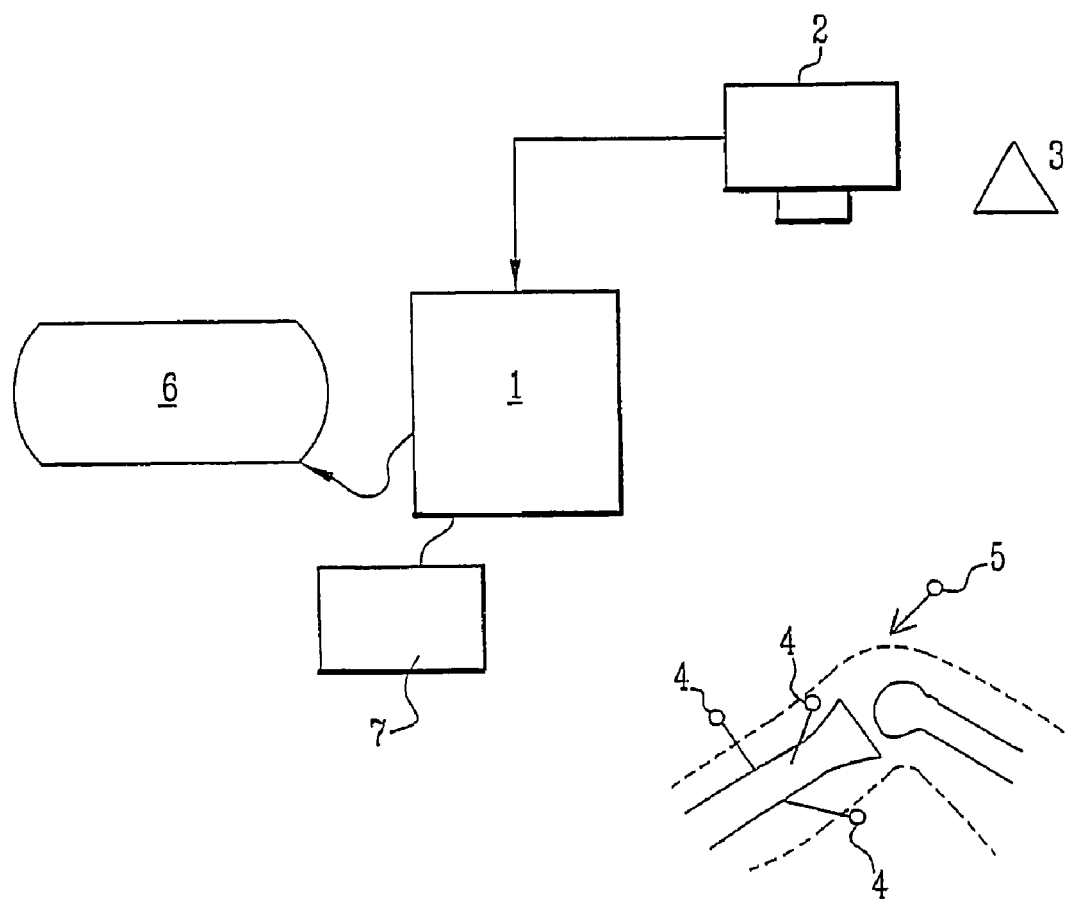

METHODS FOR SELECTING KNEE PROSTHESIS ELEMENTS AND DEVICE THEREFOR

BACKGROUND OF THE INVENTION

1. Field of the Invention

The present invention relates to a method for selecting a knee prosthesis and, more precisely, to a method of selection for choosing one or more elements of a knee prosthesis such as, in particular, a prosthetic femoral and tibial implant and/or a tibial or femoral wedge, from an available set of elements.

The method may also allow determination, on a computer model of the patient's knee, of resection planes, in particular femoral and tibial resection planes, intended to serve as a seat for the corresponding portion of the knee prosthesis.

The invention also relates to a device for carrying out this method.

2. Description of the Related Art

In conventional operations for inserting knee prostheses, the surgeon makes tibial and femoral osseous cuts depending on the patient's anatomical characteristics and the type of commercially available prosthesis, then, during insertion, makes adjustments, for example using wedges or even by remaking a resection incision to optimise as far as possible the articular properties of the prosthesis when it is in operation.

It will be appreciated that this optimisation depends greatly on the expertise of the surgeon and the anatomical features of the knee to be operated on.

The objective sought is to obtain, if possible, equal tension in the soft portions of the knee at 0 and 90° which are maintained over the entire arc of flexion of the prosthesis, satisfactory geometric alignment and extension without flexum to optimise the stresses in the standing position and obtain the most appropriate result for the patient's anatomy. A significant objective is to obtain good stability of the knee by appropriate equilibrium of the ligaments.

For this purpose, it has already been proposed that the surgeon be assisted by computerised measuring means and measurement data processing means.

It is accordingly known to store the anatomical configuration of the distal end of the patient's femur and the proximal end of the tibia on the basis of measurement data obtained by any means. This data may be obtained, for example, by scanning or preferably by in situ measurement. It is possible to use, in a three-dimensional spatial reference system defined using reference markers (for example, reflective reference beads), infrared or magnetic rays fixed at three suitable positions on a knee epiphysis, by displacement of a probe which is also marked in space by the acquisition means, software of a known type for reconstituting the precise three-dimensional shape of the ends in question. More precisely, a device of this type comprises a locating transceiver such as a high-definition infrared camera for marking fixed reference points on the patient and the marked instruments used, such as the pointer or probe, cutting guide, etc., storage and calculating means such as a computer employing 3D type modelling software, preferably a display means such as a screen, and a control means such as a mouse or tactile screen or preferably a pedal actuated by the surgeon's foot.

Suitable marking on the portion of the knee which moves relative to the reference system also allows calculation of the relative positions of the femur and the tibia.

It is thus known, after resection of the tibial plate and optionally insertion of a prosthetic tibial plate supporting element, and while using a tensor introduced by the surgeon into the space between the tibial end and the femoral articular end, to determine, under the chosen tension value imposed by the tensor, the distance between the tibia and the femur as well as the HKA angle, in other words the angle, taken internally, between the femoral mechanical axis (defined by the centre of the hip and the centre of the knee) and the tibial mechanical axis (defined by the centre of the knee and the centre of the ankle), on the one hand, when extended or in a position as close as possible to extension and, on the other hand, when flexed at 90°, the surgeon then choosing the most suitable constituent prosthetic elements from the set of available elements, this choice being able to be displayed on the screen prior to insertion, by modelling the position of the preselected element of which the characteristics have been stored in the computer.

It is noted, however, that this technique does not always allow optimal choice and/or positioning of the selected prosthetic element(s), and this prevents optimum biomechanics, particularly during retraction of the soft posterior portions of the knee in flexum and in the phases of intermediate flexion between 0 and 90° and beyond 100°. The optimum biomechanics correspond to "good tension" of the soft portions over the entire sector of movement, namely stability tension for the supporting zones and micro-play of laxity between 20 and 140°, allowing easy mobility without hypertension or uneven or exaggerated laxity.

BRIEF SUMMARY OF THE INVENTION

The present invention proposes to overcome these drawbacks and to improve the possibilities for selecting the prosthetic element(s) so as to allow optimum functioning of the knee prosthesis in all the natural positions of extension and flexion and, in particular, while allowing laxity which is of an appropriate value while remaining substantially constant over the entire range of mobility of the prosthesis.

A further objective is to determine, on the computer model of the knee, the optimum positions for the cutting planes for resection of the distal femoral end and/or proximal tibial end.

The invention relates to a method for selecting one or more knee prosthesis elements and, in particular, a prosthetic femoral portion, and/or a tibial prosthetic plate from an available set of these elements, and/or a femoral or tibial thickness template, wherein spatial data concerning the tensioned femoro-tibial spacing and position is acquired with the knee cap in position or dislocated, including the corresponding HKA angle, for at least three angular positions of the knee, namely an intermediate position flexed by approximately 20°, an extended position, if possible with 0° degrees of flexion, and a significantly flexed position, preferably with flexion of approximately 90°, the information thus obtained, corresponding to the aforementioned position with reduced flexion of 20° and the extended position, is processed to indicate whether, in these two positions, the HKA angles are substantially equal and are within the tolerable limits of *genu varum* and of *genu valgum*, and this data, in particular the data corresponding to the extension and significant flexion of approximately 90°, is processed to determine the sizes and/or the positions of the implant and, in particular, the choice of the thickness of the tibial insert for optimum filling of the space between the prosthetic condyle and the tibial cut, and the choice of the size of the femoral implant.

BRIEF DESCRIPTION OF THE DRAWING FIGURE

FIG. 1 shows a schematic view of a device according to the invention.

DETAILED DESCRIPTION OF THE PREFERRED EMBODIMENTS

The term "angle of intermediate flexion" denotes an angle of approximately 20°±10° and preferably of 20°±5°; this angle is hereinafter called 20°.

The angle in extension is preferably 0°±10°, in particular 0°±5°; this angle is hereinafter called 0°. The angle of great flexion, preferably 90°, may be 90°±15°, in particular 90°±10°, preferably 90°±5°; this angle is hereinafter called 90°.

In a particularly preferred embodiment of the invention, the data is acquired in the following order: data at 20°, then data at 0°, then data at 90°.

According to the invention, it is verified by means of a computer that the angles at which the data is acquired actually correspond to the aforementioned angles, acquisition being denied if the corresponding angle is not observed.

The acquisition and processing of data corresponding to the intermediate angle of 20° and to the angle of extension at 0° may be used by the surgeon to consider whether the anatomical properties of the knee are suitable, or to reduce a possible flexum (inability to obtain complete extension) or else to achieve appropriate liberation of the collateral ligaments in the event of exaggerated valgum-or varum.

Preferably, the method according to the invention determines whether, at extension angles and angles of flexion of 20°, the HKA angle is substantially equal in both positions and between 175° and 180° in the case of genu varum and between 180° and 184° in the case of genu valgum, and if so, the method considers that the anatomical properties are appropriate.

The scope of use of the method according to the invention also provides for the acquisition of data relating, in particular, to the femoro-tibial spacing and to the HKA angle, for other intermediate positions of flexion, in particular 45°, or even continuously. Continuous checking of the tension of the soft femur portions relative to the tibia, combined with measurement of the HKA angle between 0 and 140°, allows the correct femoro-tibial alignment to be obtained and, in particular, allows the ideal positioning of the implants to be calculated. The femur/tibia kinetics comprise, in particular a flexion-extension movement, and it is important to know the centres of rotation thereof. These may be calculated in succession between 0 and 140° by means of the invention. Knowledge of these so-called "anatomical" centres of rotation will facilitate determination of the position of the so-called "prosthetic" centres of rotation relative to the drawing of the prosthesis. In the context of the invention, however, the collected data comprises at least that which corresponds to the angles of 0° (or extension), reduced flexion and significant flexion, and the processing means used in the method verify that the measurements taken actually correspond to these angles, as retrieved by the processing means used in the method.

According to a preferred embodiment of the invention, the processing relating to the determination of the most appropriate elements of the prosthesis of the method is not carried out until the data corresponding to 0 and 20° are acceptable, namely absence of substantial flexum and HKA angles which are substantially equal and within the permitted values. Once these verifications have been made, the computer processing models the articulation by incorporating therein the dimensional data relating to the various previously stored components of the sets of prostheses to form models of the knee with prostheses in the implanted position.

This modelling ensures that the antero-posterior position of the femoral prosthesis is such that:

the upper edge of the prosthetic trochlea is in contact with the anterior femoral cortical bone or is slightly posterior if the actual size of the patient's femur falls between two prosthetic sizes;

the axial rotation of the femoral prosthesis is such that the posterior prosthetic condyles are parallel to the actual tibial cut, the tibial insert selected from the set best fills the space between the prosthetic condyles and the tibial cut;

the medio-lateral position is such that the implant is centred on the anatomical notch, and the distal position of the femoral implant is chosen using the selected tibial plate and the extended position is stored so that the femoral implant makes good contact with the determined tibial insert in flexion without residual laxity in the extended position;

the femoral varus is such that, when extended, the distal prosthetic condyles are parallel to the tibial cut produced;

the femoral flexum is substantially zero.

This optimisation by modelling may be entirely automatic, in which case the method indicates to the surgeon the exact choice of the various elements of the prosthetic set. Owing to the recording of the positions of the femoral distal cut and the tibial proximal cut between 0 and 140°, after choice of the cuts and the implants, functioning of the knee between 0 and 140° may be simulated on a screen.

This stage allows hypertension or excessive laxity of between 0 and 140° to be eliminated. Software allows the optimum position of the femur and tibia implants and therefore the cuts to be defined so as to harmonise with one another or preferably with the anatomy and the soft portions.

In a further embodiment, the method enables the surgeon to preselect parameters inherent in the set, such as the size of the femoral implant, the height of the tibial insert, the axial rotation, the femoral varus, the flexum, the antero-posterior position, the lateral position, and the height of the distal femoral cut to be made.

Advantageously, the internal and external laxities estimated in flexion and in extension are displayed continuously, at least for the aforementioned three positions and preferably over any modelled flexed position.

The invention also relates to a device for carrying out the method according to the invention, said device comprising: a means for acquiring the spatial position of a three-dimensional spatial system of reference marks on the patient's tibia or femur and spatial positions of marks, probes or instruments on the other bone to obtain spatial data relating to the displacement between the patient's femur and tibia in the knee region, means preferably comprising previously obtained anatomical data on a patient's femur and/or tibia, for determining, as a function of said spatial data, the angle of flexion between the femur and the tibia, the distance between the ends of the femur and tibia, as well as the HKA angle, processing and storage means for storing said distance and said HKA angle in combination with the angle of flexion for at least three angles of flexion, namely an angle of reduced flexion, in particular, of 20°, as defined above, an angle of extension, in particular an angle of 0°, as defined above, and an angle of significant flexion, in particular an angle of 90°, as defined above, means for comparing said distances and HKA angles, at least for the angle of reduced flexion and the angle of extension, storage means comprising dimensional data relating to sets of knee implant components, 3D processing means for modelling the implanted positions of said elements of implant prosthesis set, at least in the positions of angles of extension and of great flexion, and processing means for providing relevant data relating to the modelled knee implant and/or for selecting said elements of the implant set providing the best characteristic data, means for displaying said data or for selection, and means for controlling operation of the device.

Said control means are preferably designed to enable the operator to record the collected data corresponding at least to said angles of slight flexion, of extension and of pronounced flexion, in combination with the processing means verifying and validating the correct value of the angle for recording.

Preferably, said control means also allow the operator to choose one or more elements of a set of prosthetic elements so as to allow said processing means to model the implantation of said elements and to provide or process the relevant characteristics for said elements in the implanted modelling position.

Preferably, the control means comprise foot-actuated or voice-actuated means or means designed in another way to enable a surgeon to control the device without having to use his hands.

The acquisition means for collecting spatial data relating to the displacements and to the relative positions of the femur and the tibia preferably comprise a high-definition digital camera which is sensitive to the signals originating from the osseous portions of the knee, such as, for example, infrared reflective markers or optionally image detecting means.

The 3D modelling means may be commercial software packages adapted, if necessary, to the modelling of osseous portions.

The processing means employ the following acquisitions and processing:
acquisition of the anatomical marks required for the mechanical axis (centre of hip and ankle),
acquisition of various anatomical points in the knee region,
acquisition and modelling of the tibial surface,
tibial planning,
positioning of the guide, fixing and tibial cut,
verification of the planeness of the tibial cut,
tension and acquisition at 20°,
tension and acquisition at 0°,
comparison of the two values and decision,
tension and acquisition at 90°,
femoral planning,
positioning of the femoral cutting guides, fixing and cuts.

The invention also relates to a method of inserting an articular knee prosthesis comprising the succession of the following procedures:
conventional acquisition of the anatomical marks required for the mechanical axis, in particular centre of hip and ankle,
setting of reference markers on osseous portions of the knee and conventional acquisition of these anatomical points,
acquisition and modelling of the tibial surface,
tibial planning, namely determination of the tibial implant and its position,
positioning and fixing of a tibial cutting guide and resection by cutting of the tibial plate, optionally insertion of a prosthetic tibial plate base,
verification of the planeness of the tibial cut,
distraction by tensor of the femoro-tibial interval in at least two angular positions, namely a position flexed by 20°, as defined above, and an extended position,
obtaining of the osseous distances and of the HKA angle for the two positions by the method of selection according to the invention,
if necessary, posterior liberation in the event of flexum and/or liberation of collateral ligaments until suitable HKA angles are obtained in said positions, this verification being carried out by the method of selection according to the invention,
distraction with high flexion, in particular of 90°, with tensor and obtaining of corresponding osseous distances and HKA angle,
femoral planning including:
manual preselection of various implant elements as a function of the results of said measurements and verification of the values obtained by modelling,
and/or obtaining of automatic selection of said elements with indication of said relevant characteristics, and
positioning of the femoral cutting guides, fixing, cutting and implantation of the selected element(s).

Further advantages and characteristics of the invention will emerge from reading the following description which is given by way of a non-limiting example with reference to the accompanying drawing, in which the single figure is a schematic view of a device according to the invention.

The device according to the invention comprises a computer 1 for carrying out the method according to the invention. It also comprises a high-definition digital camera 2 combined with a source of infrared emission 3 covering the field in which there evolve one or more assemblies of three markers 4, which passively send back the infrared radiation. In a manner known per se, a group of three markers is set by the surgeon on a limb or on a bone, for example on the inferior portion of the femur to form a three-dimensional marking system which enables the camera-computer unit to determine in the conventional manner the exact geometric location of one or more additional markers 5 placed, for example, on an osseous portion which moves relative to the reference system of the three markers. Devices of this type are well-known in the field of analysis of shapes and computer modelling and do not need to be described in more detail here, the modelling software packages also being commercially available. For example, a device of this type enables a surgeon, who is appropriately displacing the movable marker on an anatomical surface, to reproduce this surface by modelling.

The modelling software used in the present invention is designed in a manner known per se to allow calculation, relative to the spatial reference system of the three sensors positioned on one of the bones of the joint, of the exact position of the other bone of the joint and, in particular, the angle of flexion between the two bones and therefore the two portions of the inferior member, the distance between the two bones, the lateral and antero-posterior displacements and the relative rotations.

The device further comprises a screen 6 which is capable of displaying the results of the processing of the spatial data by the computer as well as the various other relevant elements of the software so as to be able to be viewed by the surgeon, and a control device 7 which may be, for example, a conventional computer keyboard or the screen 6 in the form of a tactile screen or else, preferably, a pedal-operated control device which may be operated by the surgeon's foot.

The method according to the invention is carried out in the following manner:

The surgeon has a sterile set of implants of various sizes, each implant conventionally comprising: a tibial component formed by a base cooperating with a tibial rod in order to seal the base perfectly on the cutting surface of the tibial plate with, for each type of base, a set of tibial plates made, for example, of polyethylene which may be attached to the base to provide the tibial prosthetic articular surface; a femoral component comprising a distal end which cooperates with a femoral rod intended to form a seal in the femoral medullary channel, with a prosthetic trochlea part which is intended to be articulated with the tibial plate, this part being either directly connected to the femoral distal end or, in other models, being capable of being attached there, for example by interposition of wedges of a set of wedges of variable thicknesses, the tibial component and a femoral component further being joined in an articular manner by a pivoting means.

After having positioned the various infrared markers, then having acquired the anatomical shapes of the relevant portions of the femur and the tibia and having obtained the exact anatomical modelling of these shapes and dimensions using a computer (or in a variation, these dimensional data may have already been introduced into the computer beforehand, for example by preoperative scanning), the surgeon performs the resection of the impaired tibial plate and, using the moving marker, marks the position of this cutting plane which is incorporated into the computer model.

Preferably, the computer screen continuously displays the value of the current flexion on a lateral view of the knee throughout the operation. The HKA angle is also permanently displayed on a front view.

The surgeon then proceeds to the following stages after tibial resection:

The surgeon flexes the knee by 20°. When the flexion is approximately 20° (tolerance of ±5°), the surgeon inserts the tensor and places the knee under satisfactory tension.

He actuates the control means 7 and the camera-computer unit acquires and stores all the relative position data between the femur and the tibia at this angle.

In a second phase, the surgeon brings the knee to approximately 0° of flexion, in other words in extension. When this value is achieved (with tolerance of ±5°), the surgeon inserts the tensor and places the knee in satisfactory extension.

He again actuates the control means 7 and the camera-computer unit acquires and stores all the data of the relative position of the femur and the tibia.

At each actuation, the camera-computer unit verifies that the angle of flexion is actually 20°±5° then 0°±5°. The data relating to said positions, namely the laxity or, more precisely, the internal and external laxity in the region of the respective internal and external condyles and the HKA angle, are stored and associated with the corresponding angle.

The software then compares the value of the HKA angle at 20° and the value of the HK angle at 0°. It also checks that this angle is between 175 and 180° in the case of genu varum and between 180 and 140° in the case of genu valgum.

If these two conditions are satisfied and there is no problem of flexum, the surgeon continues. He proceeds to the following stage by flexing the knee to approximately 90° of flexion.

If, on the other hand, one of these conditions is not satisfied, he performs posterior liberation in the case of flexum and recommences measurement around 20° then around 0° until the two stages provide substantially identical HKA values; if this is not the case, he proceeds to liberate the collateral ligaments in the conventional manner until the appropriate result is obtained.

When these criteria have been satisfied, and after having placed the knee at 90°, he again inserts the tensor and places the knee under satisfactory tension.

The relative positions of the tibia and femur are also stored at the angle of 90° by the surgeon's action on the control means.

Once these different acquisitions have been made, the computer is in a position to automatically propose the position of the femoral implant and its rotational orientation, as well as the height of the tibial insert to be chosen, taking the following criteria and constraints into consideration:

the position of the prosthetic femoral trochlea in the antero-posterior plane is obtained by contact between the upper edge of the prosthetic trochlea and the anterior femoral cortical bone;

the axial rotation (in the femoral stem) of the femoral component is such that the posterior prosthetic condyles are parallel to the tibial cut which has been produced;

the thickness of the tibial insert (base and tibial plate) is chosen for optimum filling of the space between the prosthetic condyles and the tibial cut without being greater than this space. If the slimmest tibial insert is still greater than the available space, the software will enable the theoretical position of the tibial cut to be produced to be obtained, to allow positioning of this insert;

the medio-lateral position is such that the implant is centred on the anatomical notch between the anatomical condyles;

the distal position of the implant is calculated using the chosen tibial plate and the balanced extended position which has previously been stored. The distal cut height is such that, in the extended position, the femoral implant is in contact with the tibial insert found to be in flexion? This is a constraint which applies to the laxity in extension.

The femoral varus is such that, in extension, the distal prosthetic condyles are parallel to the tibial cut produced.

The femoral flexum is zero, the femoral cutting angle relative to the perpendicular to the femoral-mechanical axis in profile being determined as a function of the type of prosthesis, certain types allowing for an angle other than zero, for example 15°.

For each position, the screen indicates the angle of flexion, the internal and external laxity and the HKA angle.

The proposal which is thus made by the device according to the invention may be modified by actuating the control means 7, for example to modify the following parameters:

size of the femoral implant (six sizes are generally available)

height of the insert (generally from 10 to 20 mm), axial rotation, femoral varus, flexum, antero-posterior position,

The invention claimed is:

1. A method for selecting one or more knee prosthesis elements, comprising:

tensioning femoro-tibial spacing and acquiring with acquiring means spatial data concerning the tensioned femore-tibial spacing and position with a knee cap in position or dislocated, including a corresponding HKA angle, for at least three angular positions of the knee, including an intermediate position, an extended position if possible with 0° degrees of flexion, and a significantly flexed position;

processing with determining means the data thus obtained, corresponding to the intermediate position and the extended position, to indicate whether, in these two positions, the HKA angles are substantially equal and are within tolerable limits of genu varum and of genu valgum; and processing with processing means the data corresponding to the extension and significant flexion to determine sizes and/or positions of an implant and, or a choice of a thickness of a tibial insert for optimum filling of a space between a prosthetic condyle and a tibial cut or a choice of the size of a femoral implant.

2. The method according to claim 1, wherein the angle of flexion at the intermediate position is 20°±10°.

3. The method according to claim 1, wherein the angle when extended is 0°±5°.

4. The method according to claim 1, wherein the angle of significant flexion is 90°±15°.

5. The method according to claim 1, wherein the data is acquired in the following order:

data at 20°, then data at 0°, then data at 90°.

6. The method according to claim 1, further comprising verifying by means of a computer that the angles at which the data is acquired actually correspond to desired angles, acquisition being denied if the corresponding angle is not observed.

7. The method according to claim 1, further comprising determining whether, at extension angles and angles of flexion of 20°, the HKA angle is substantially equal in both positions and between 175° and 180° in the case of genu varum and between 180° and 184° in the case of genu valgum, and if so, considering whether anatomical properties are appropriate.

8. The method according to claim 1, wherein processing relating to determination of most appropriate elements of the prosthesis of the method is not carried out until the data corresponding to 0° and 20° are acceptable, as indicated by absence of substantial flexum and HKA angles which are substantially equal and within permitted values.

9. The method according to claim 1, wherein said data is processed by modelling means to determine an antero-posterior position of a femoral prosthesis such that:

an upper edge of a prosthetic trochlea is in contact with an anterior femoral cortical bone;

an axial rotation of a femoral prosthesis is such that posterior prosthetic condyles are parallel to an actual tibial cut, the tibial insert selected from the set best fills a space between the prosthetic condyles and the tibial cut;

a medio-lateral position is such that the implant is centred on an anatomical notch, and a distal position of the femoral implant is chosen using a selected tibial plate and the extended position is stored so that laxity is substantially zero in the extended position;

a femoral varus is such that, when extended, the distal prosthetic condyles are parallel to the tibial cut.

10. The method according to claim 1, wherein a result of the processing indicates an exact choice of various elements of a prosthetic set.

11. The method according to claim 1, wherein the method further comprises preselecting by means of controlling parameters inherent in the set, including a size of the femoral implant, a height of the tibial insert, axial rotation, femoral varus, flexum, antero-posterior position, lateral position or a height of a distal femoral cut to be made.

12. The method according to claim 1, wherein internal and external laxities estimated in flexion and in extension are displayed continuously, at least for the three angular positions.

13. The method according to claim 1, wherein the knee prosthesis elements comprise at least one of a prosthetic femoral portion, a tibial prosthetic plate or a femoral or tibial thickness template.

14. The method according to claim 1, wherein the significant flexed position has a flexion of approximately 90°.

* * * * *

UNITED STATES PATENT AND TRADEMARK OFFICE
CERTIFICATE OF CORRECTION

PATENT NO. : 7,611,519 B2  Page 1 of 1
APPLICATION NO. : 10/494615
DATED : November 3, 2009
INVENTOR(S) : Lefevre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 850 days.

Signed and Sealed this

Twelfth Day of October, 2010

David J. Kappos
*Director of the United States Patent and Trademark Office*